US008343568B2

(12) United States Patent
Chen et al.

(10) Patent No.: US 8,343,568 B2
(45) Date of Patent: Jan. 1, 2013

(54) STENT FIXTURE AND METHOD FOR REDUCING COATING DEFECTS

(75) Inventors: Yung-Ming Chen, San Jose, CA (US);
Allan Bradshaw, Newark, CA (US);
Philip C. Foreman, San Jose, CA (US);
Greg Teaby, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 67 days.

(21) Appl. No.: 12/890,536

(22) Filed: Sep. 24, 2010

(65) Prior Publication Data
US 2011/0076386 A1    Mar. 31, 2011

Related U.S. Application Data

(62) Division of application No. 11/174,195, filed on Jun. 30, 2005, now Pat. No. 7,823,533.

(51) Int. Cl.
*A61L 33/00*    (2006.01)
(52) U.S. Cl. ....... 427/2.25; 623/1.1; 623/1.13; 623/1.54
(58) Field of Classification Search ............... 427/2.24, 427/2.25; 623/1.46, 1.42, 1.13, 1.54, 1.1
See application file for complete search history.

(56) References Cited

U.S. PATENT DOCUMENTS

| 5,520,697 | A | 5/1996 | Lindenberg et al. |
| 6,183,503 | B1* | 2/2001 | Hart et al. .................... 623/1.1 |
| 6,565,659 | B1 | 5/2003 | Pacetti et al. |
| 7,169,172 | B2 | 1/2007 | Levine et al. |
| 2004/0013792 | A1* | 1/2004 | Epstein et al. .............. 427/2.24 |
| 2004/0024442 | A1* | 2/2004 | Sowinski et al. .......... 623/1.13 |
| 2004/0172804 | A1 | 9/2004 | Hopkins |
| 2004/0194704 | A1 | 10/2004 | Chappa et al. |
| 2005/0070997 | A1* | 3/2005 | Thornton et al. ........... 623/1.46 |
| 2007/0003688 | A1 | 1/2007 | Chen et al. |

FOREIGN PATENT DOCUMENTS
WO    WO 2004/008995    1/2004

OTHER PUBLICATIONS

Search Report for PCT/US2006/023636 filed Jun. 16, 2006, mailed Nov. 9, 2006, 11 pgs.

* cited by examiner

*Primary Examiner* — Dah-Wei Yuan
*Assistant Examiner* — Andrew Bowman
(74) *Attorney, Agent, or Firm* — Squire Sanders (US) LLP

(57) ABSTRACT

A stent fixture for supporting a stent during formation of a coating is provided.

18 Claims, 5 Drawing Sheets

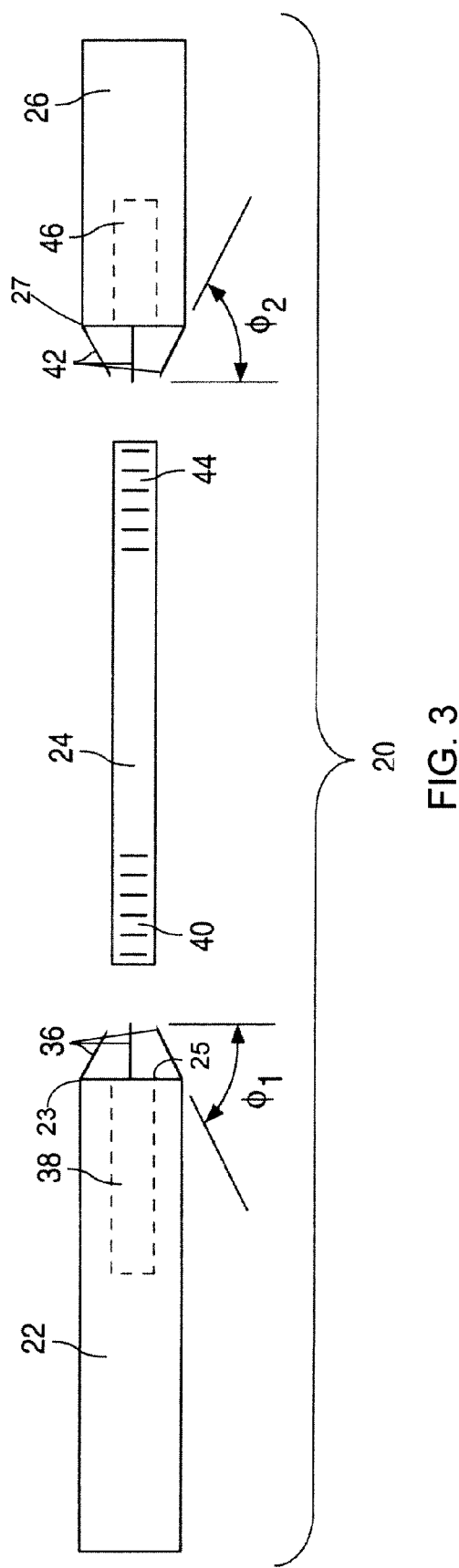

STENT FIXTURE AND METHOD FOR REDUCING COATING DEFECTS

CROSS-REFERENCE

This is a divisional application of application Ser. No. 11/174,195 filed on Jun. 30, 2005, the contents of which are incorporated by reference herein in its entirety for all purposes.

TECHNICAL FIELD

This invention relates generally to stent fixtures, and more particularly, but not exclusively, provides a stent fixture and method for reducing coating defects on stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between the adjacent struts 12, leaving lateral openings or gaps 16 between the adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent fixture and method of use are needed to minimize coating defects.

SUMMARY

In accordance with one embodiment a stent fixture for supporting a stent during formation of a coating is provided comprising a structure having arm elements extending from the structure. The arm elements can be are configured to allow an inner side of a stent to rest on and be supported by the arm elements. The structure can support one end of the stent such that the fixture can, in some embodiments, additionally comprise a second structure for support an opposing end of the stent. The second structure can comprise arm elements extending out from the second structure. The arm elements of the second structure are configured to allow the inner side of the stent to rest on and be supported by the arm elements of the second structure. In some embodiments, the fixture can include a third structure connecting the structure to the second structure and extending through a longitudinal bore of the stent. The stent can be securely pinched between the plurality of arm elements of the structures.

In accordance with another aspect of the invention, methods of coating a stent using the above-described fixtures are provided.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 3 is a diagram illustrating a disassembled view of stent fixture of FIG. 2;

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
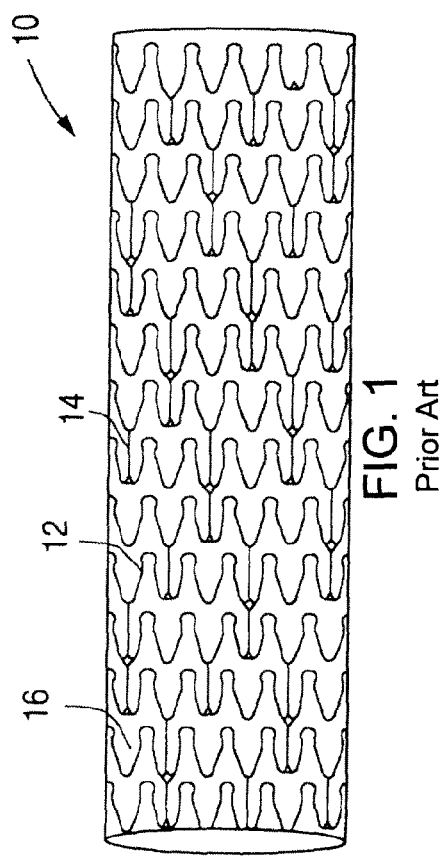
FIG. 1 is a diagram illustrating a conventional stent.
Figure 2:
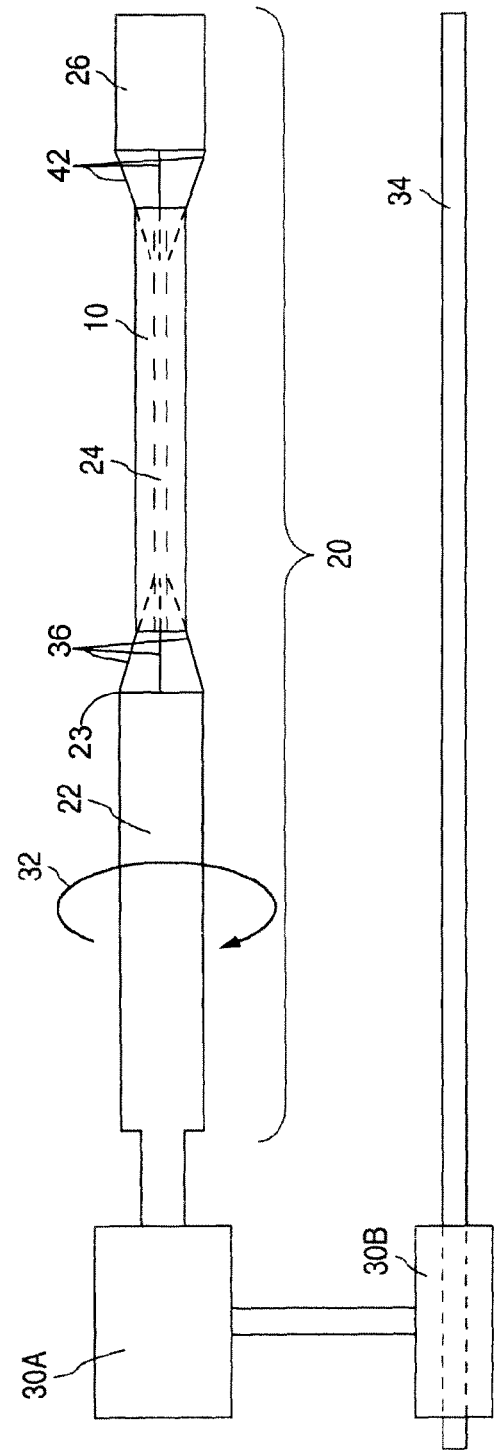
FIG. 2 is a diagram illustrating a stent fixture in accordance with an embodiment of the invention.

FIG. 2 illustrates a stent mandrel fixture 20 in accordance with an embodiment of the invention. The fixture 20 for supporting the stent 10 is illustrated to include a support member 22, a mandrel 24, and a lock member 26. The support member 22 can connect to a motor 30A so as to provide rotational motion about the longitudinal axis of the stent 10, as depicted by arrow 32, during a coating process. Another motor 30B can also be provided for moving the support member 22 in a linear direction, back and forth, along a rail 34.

Figure 5:
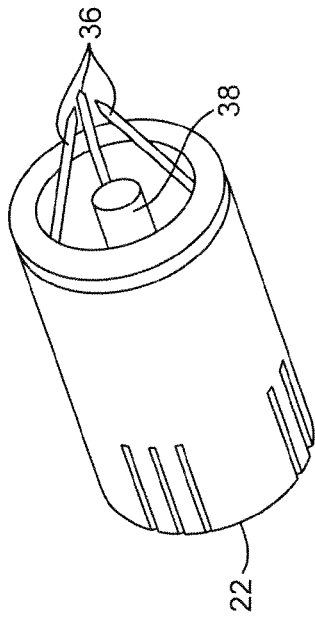
FIG. 5 is a diagram illustrating a perspective view of the support member.

FIG. 3 illustrates a disassembled view of the stent mandrel fixture 20. The support member 22, can have a generally cylindrical body and an end wall 23 which faces an end of a stent. In some embodiments, as best illustrated by FIG. 5, the end wall 23 can include a recess 25 defining an edge rim or lip protruding around the circumference of the end wall 23. A plurality of elements, support aims or wires 36 extend out from the perimeter of the support member 22, more particularly from the end wall 23. In some embodiments, the elements 36 extend out from the edge rim. The elements 36 can be, in some embodiments, tapering inwardly at an angle $\phi_1$ of about 15° to about 75°, more narrowly from about 30° to about 60°. By way of example, angle $\phi_1$ can be about 45°. If the elements are extending from edge rim of the end wall 23, an inner side of the edge rim can be slanted to accommodate for this tilt. The elements 36 can converge inwardly from an edge of the end wall 23 of the support member towards the center of the end wall 23. As is best illustrated by the figures, the elements 36 do not contact one another and allow for a sufficient entry space for the mandrel 24 to extend out from the support member 22. In other words, the spacing between the end tips of the elements 36 should be at least as wide as the diameter of the mandrel 24 used. In some embodiments, the end tip of the elements 36 can contact the mandrel 24. In other embodiments, the end tips of the elements 36 converge but yet remain spaced from the mandrel 24. The elements 36 can extend at least partially over the mandrel 24 and can prevent a stent from making contact with the mandrel. The elements 36 can also prevent the support member 22 from making contact with an end ring of the stent. The elements, wires or support arms 36 can be rigidly coupled to the support member 22 so as not be capable of pivoting about a juncture, bending or flexing when a stent is positioned thereon and/or during a coating process. Alternatively, elements 36 can have at least a partial "give" in the four of bending, flexing or pivoting. In some embodiments, at least one of the elements can be rigid while at least one is flexible, bendable or pivotable. FIG. 3 illustrates 3 elements, wires or support arms 36. In some embodiments, the numbers can be 2, 3, 5, 6, 7 or 8. Although more than 8 can be used, it may provide for excessive contact points leading to coating defects while on the other hand the amount of support is not necessarily better.

In accordance with one embodiment of the invention, the mandrel 24 can be permanently affixed to the support member 22. Alternatively, the support member 22 can include a bore 38 for receiving a first end 40 of the mandrel 24. The first end 40 of the mandrel 24 can be threaded to screw into the bore 38 or, alternatively, can be retained within the bore 38 by a friction fit. The bore 38 should be deep enough so as to allow the mandrel 24 to securely mate with the support member 22. The depth of the bore 38 can also be over-extended so as to allow a significant length of the mandrel 24 to penetrate or screw into the bore 38. The bore 38 can also extend completely through the support member 22. This would allow the length of the mandrel 24 to be adjusted to accommodate stents of various sizes.

The outer diameter of the mandrel 24 can be smaller than the inner diameter of the stent 10, as positioned on the fixture, such that the elements 36 prevent the outer surface of the mandrel 24 from making contact with the inner surface of the stent 10. A sufficient clearance between the outer surface of the mandrel 24 and the inner surface of the stent 10 should be provided to prevent the mandrel 24 from obstructing the pattern of the stent body during the coating process. By way of example, the outer diameter of the mandrel 24 can be from about 0.010 inches to about 0.040 inches when the stent 10 has an inner diameter of between about 0.025 inches and about 0.065 inches, e.g., for a coronary stent. For a peripheral stent having a larger diameter, the mandrel 24 can have larger diameters.

In some embodiments, the lock member 26 can be identical or generally similar to the support member 22. In some embodiments, the lock member 26 includes a plurality of elements, support arms or wires 42 extending out from an end wall 27 of the cylindrical body of the lock member 26. As with the elements 36 of the support member 22, elements 42 of the lock member 26 can be rigid, flexible, bendable, pivotable or any combination. In some embodiments, elements 36 can be more or less flexible, bendable or pivotably than the elements 42 of the lock member 26. Preferably, the degree of flexibility or rigidness is the same. In some embodiments, elements 42 can have an inwardly tapered angle $\phi_2$. Angle $\phi_2$ can be the same as or different than the above-described angle $\phi_1$. Although 3 elements 42 have been illustrated, any suitable number such as 2, 4, 5, 6, 7, and 8 can be used. More than 8 can be used but may increase the contact areas between a stent and elements 42. A second end 44 of the mandrel 24 can be permanently affixed to the lock member 26 if the end 40 is disengagable from the support member 22. Alternatively, in accordance with another embodiment, the mandrel 24 can have a threaded second end 44 for screwing into a bore 46 of the lock member 26. The bore 46 can be of any suitable depth that would allow the lock member 26 to be incrementally moved closer to the support member 22. The bore 46 can also extend completely through the lock member 26. Accordingly, the stents 10 of any length can be securely pinched between the support and the lock members 22 and 26. In accordance with yet another embodiment, a non-threaded second end 44 and the bore 46 combination is employed such that the second end 44 can be press-fitted or friction-fitted within the bore 46 to prevent movement of the stent 10 on the stent mandrel fixture 20.

Figure 6:
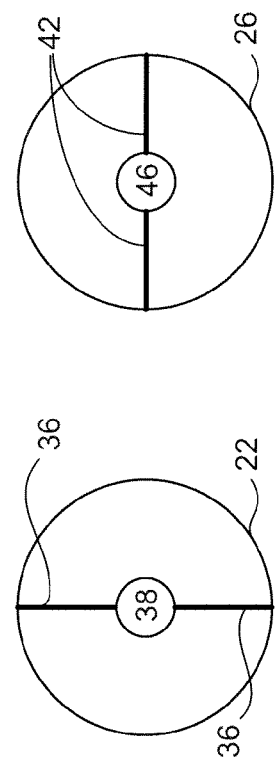
FIG. 6 is a diagram illustrating a stent mounted on the support member.

During a spray coating process, the stent 10 rests on and/or is supported by the elements, support anus or wires 36 and 42, as will be discussed in further detail in conjunction with FIG. 6 and FIG. 9 below. In an embodiment of the invention, the elements, support arms or wires 36 and 42 may have diameters of about 0.004 inches to about 0.006 inches. In some embodiments, the diameter of the wires is of sufficient size so as to allow for the wires to be fittingly placed in a crown of the end rings of a stent, as is best illustrated by FIG. 6. For example, an end ring of a stent can have a "V" shape, a "U" shape, a unique configuration to the struts. The elements 36 and 42 can be of small enough diameter so as to be placed at least partially in between the strut bodies or the space between two segments of the struts. As such, the stent 10 is only in contact with the elements, support arms or wires 36 and 42 and therefore provides minimal contact area for the collection of excess coating, thereby minimizing the formation of clumps, which can lead to further defects, such as tears and rough surfaces, when the stent 10 is removed from the fixture 20.

In order to further reduce coating defects, the elements, support arms or wires 36 and 42 may be coated with or made of, via injection molding, one or more polymeric materials having less adhesive force with the coating substance than with the elements, support arms or wires 36 and 42. Examples of a suitable polymeric materials include poly (tetrafluoroethylene) (e.g., TEFLON), fluorinated ethylene propylene ("FEP"), poly (vinylidene fluoride) ("PVDF"), poly (para-xylyene), polyolefins (e.g., high density poly (ethylene) and poly (propylene)), and ME92 coating from ME92 Operations, Inc. of Providence, R.I. In an alternative embodiment of the invention, the elements, support arms or wires 36 and 42 may be made of one or more of the non-stick polymeric materials.

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodable. Biostable refers to polymers that are not biodegradable. The teams biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy) propyl-rapamycin, 40-O-[2-(2-hydroxy)ethoxy]ethyl-rapamycin, and 40-O-tetrazole-rapamycin.

Figure 4:
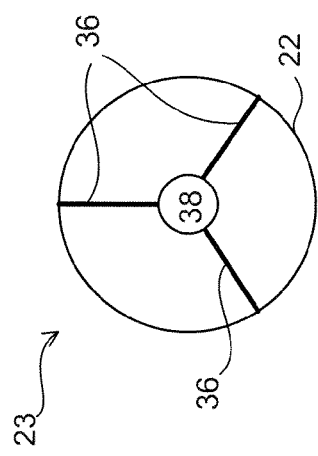
FIG. 4 is a diagram illustrating a front view of a support member of the stent fixture of FIG. 2.

FIG. 4 is a diagram illustrating a front view of the end wall 23 of the support member 22 (which can be similar to the end wall 27 of the lock member 26) of the stent mandrel fixture 20 (FIG. 2). The plurality of elements, support arms or wires 36 includes 3 wires spaced 120° apart from each other. The plurality of wires 36 extend from the circumference of the support member 22 to the bore 38. In other embodiments, the plurality of wires 36 can be spaced apart differently and/or comprise a different number of wires 36.

FIG. 5 is a diagram illustrating a perspective view of the support member 22 (which can be similar to that of the lock member 26). In an embodiment of the invention, the plurality of wires 36 may have pointed ends such that the sections of the ends facing the mandrel 24 run parallel with the mandrel 24, which enables a smoother fit between the mandrel 24 and the wires 36.

FIG. 6 is a diagram illustrating the stent 10 mounted on the stent mandrel fixture 20. When the stent 10 is mounted, the elements, support arms or wires 36 and 42 contact the mandrel and the stent 10 is supported by the wires 36 as well as the wires 42. As such, the stent 10 only interfaces with the stent mandrel fixture 20 at six minute points, thereby limiting the area at which clumps can form. Further, the support member 22 can include a lock pin 65 that extends from a surface of the member 22 through to the mandrel 24 for locking the mandrel in place.

Figure 7:
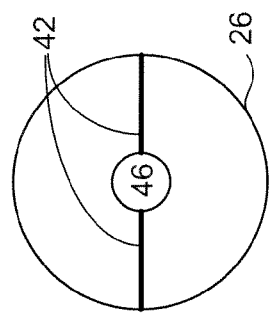
FIG. 7 is a diagram illustrating a support member and locking member according to another embodiment of the invention.

FIG. 7 is a diagram illustrating a support member 22 and a locking member 26 according to another embodiment of the invention. The support member 22 and the locking member 26 each have two wires extending there from. When the stent 10 is mounted to the members 22 and 26, one of the members is rotated 90° with respect to the other to ensure that the stent 10 is adequately supported, as is shown.

Figure 9:
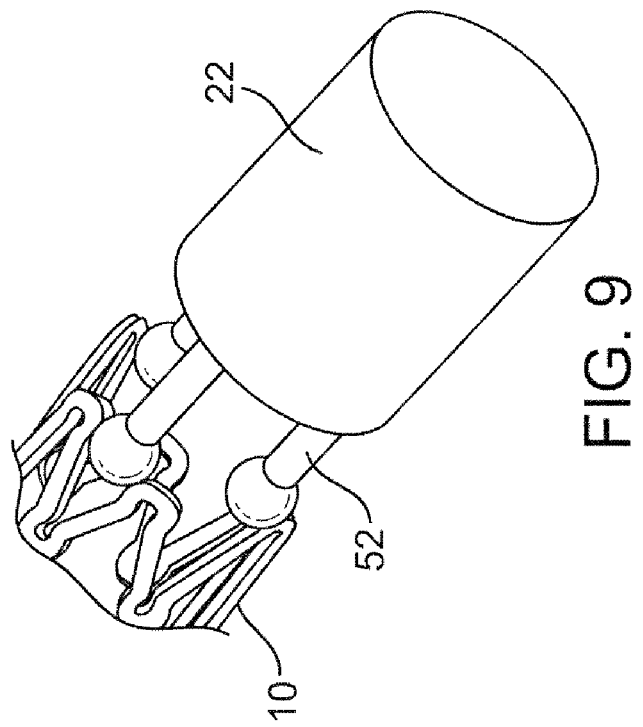
FIG. 9 is a diagram illustrating a stent mounted to the support member of FIG. 8.
Figure 8:
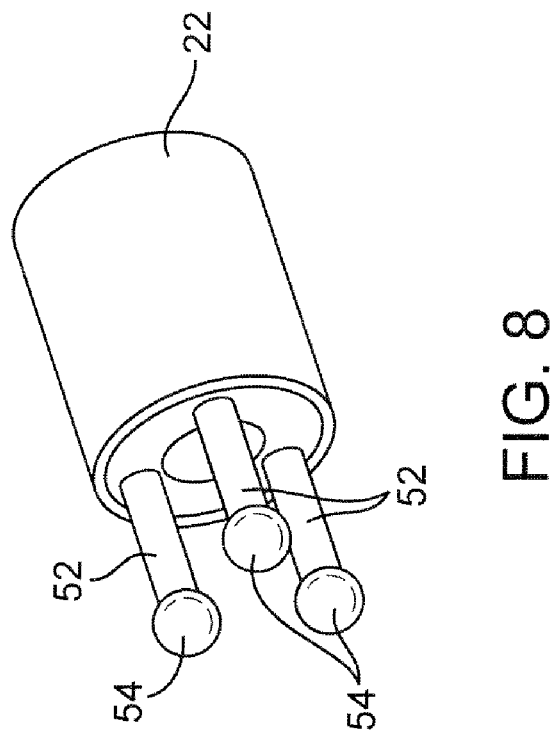
FIG. 8 is a diagram illustrating a support member according to another embodiment of the invention.

FIG. 8 and FIG. 9 are diagrams illustrating a support member 22 according to another embodiment of the invention. The support member 22 of FIG. 8 and FIG. 9 has a plurality of elements, support arms or wires (e.g., 3) 52 extending laterally from the support member 22. The elements can extend parallel to the longitudinal axis of a stent or parallel to the longitudinal axis of the mandrel 24. The elements, support arms or wires 52 may be about 4 to about 8 mm in length and about 0.004 to about 0.008 inches in diameter. The elements, support arms or wires 52 each have a sphere 54 at their respective ends. In some embodiment, the spheres 54 are large enough so as to prevent the inner side of a stent from making contact with the element 52. In one embodiment, the size of the spheres 54 should be larger than a gap between the struts under which the spheres are placed and small enough so that no portion of the spheres 52 protrudes out of the outer surface of the stent. In some embodiments, a portion of the spheres can protrude out from the outer surface of the stent. By way of example, the spheres 54 can each have a diameter of about 0.015 to about 0.020 of an inch. The spheres 54 provide more rigid support than the wires 36 or 42 but provide more contact surface for a coating composition to pool, thereby slightly increasing the possibility of coating defects but still providing less surface area than conventional stent mounting fixtures.

In some embodiments, elements 36, 42 and/or 52 can extend starting from an inner position of the end wall of the support member 22 or lock member 26 to the edge of the end wall. In essence, this would be the opposite of the embodiment illustrated by FIG. 3. In this embodiment, the elements would be extending or branching outward, away from one another. The use of the mandrel 24 in this embodiment, as well as the other embodiments described above, can certainly be optional, although preferred as a second motor may be required to be coupled to the lock member 26.

Figure 10:
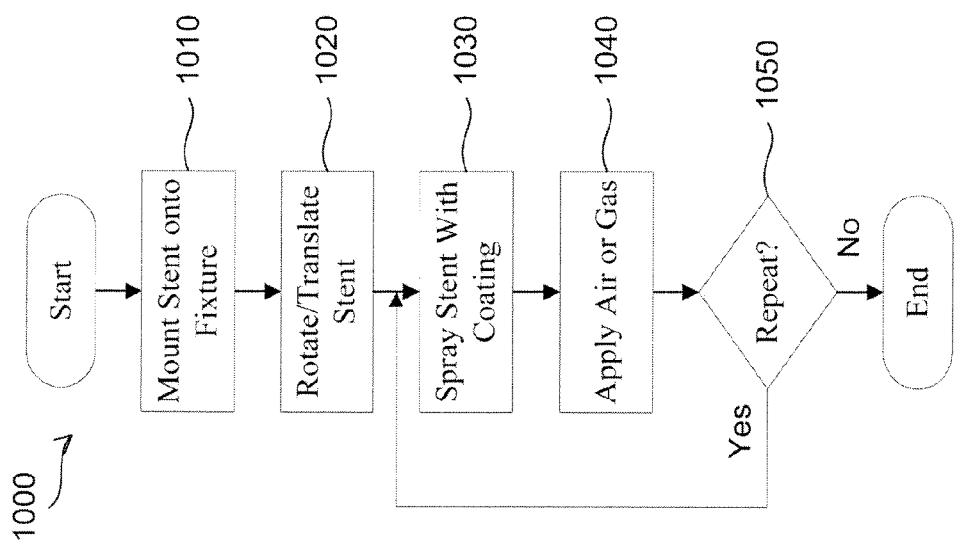
FIG. 10 is a flowchart illustrating a method of coating a stent.

FIG. 10 is a flowchart illustrating a method 1000 of coating a stent. First a stent 10 is mounted (1010) on the stent mandrel fixture 20. Mounting (1010) can include rotating the support member 22 vertically, inserting the mandrel 24 into the bore 38, mounting the stent 10 on the wires 36 or 52, and repeating for the lock member 26. A high magnification video device can also be used during the mounting (1010) to assist in adjusting the contact position between the wires 36 or 52 and the stent 10. The stent 10 is then rotated and/or translated (1020) and a coating is sprayed (1030) on the stent 10 during the rotation (1020). The rotation ratio of the mandrel and stent is 1:1 considering how elements 36 and 42 engage and rotate the stent. Air or gas can be applied (1040) to the stent for drying during and/or subsequent to the application of the coating composition. Acts of spraying and blowing can be repeated if desired (1050). The method 1000 then ends.

Figure 11:
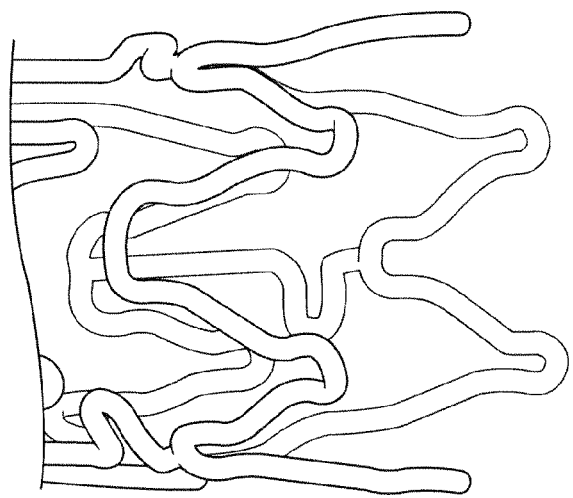
FIG. 11 is a diagram illustrating a stent coated using the stent mandrel fixture of FIG. 3.

FIG. 11 is a diagram illustrating a stent 10 coated using the stent mandrel fixture 20. As can be seen, there are no defects, such as inner diameter tearing, rough surfaces, cob webs, etc., at the end of the stent 10.

The foregoing description of the illustrated embodiments of the present invention is by way of example only, and other variations and modifications of the above-described embodiments and methods are possible in light of the foregoing teaching. For example, the plurality of wires 52 may also be coated with a non-stick polymeric material having less adhesive force with the coating substance than with the members.

What is claimed is:

1. A method for coating a stent having a bore, a longitudinal axis, and a first end and second end, comprising:
   providing elongate arm elements extending as cantilevers from a surface;
   supporting the stent upon the arm elements such that the arm elements are disposed proximal the first end and distal the second end, extend at least partially through the bore of the stent from the first end and at least a portion of the arm elements make direct contact with a luminal surface of the stent;
   rotating the stent about the longitudinal axis while the stent is supported by the arm elements; and
   spraying the rotating stent with a coating substance.

2. The method of claim 1, wherein the arm elements include arms extending at an acute angle from the surface.

3. A method for coating a stent having a bore, a longitudinal axis, and a first end and second end, comprising:
   providing elongate arm elements extending as cantilevers from a surface, wherein the arm elements include parallel arms with spheres at the ends to support the stent;
   supporting the stent upon the arm elements such that the arm elements are disposed proximal the first end and distal the second end, extend at least partially through the bore of the stent from the first end and at least a portion of the arm elements make direct contact with a luminal surface of the stent;

rotating the stent about the longitudinal axis while the stent is supported by the arm elements; and spraying the rotating stent with a coating substance.

4. A method for coating a stent having a longitudinal axis, comprising:
supporting the stent on elongate arm elements extending as cantilevers from a surface of a support member, the support member being coupled to a motor;
rotating the stent about the longitudinal axis while the stent is supported by the arm elements; and
applying a coating to the stent, including the steps of
spraying the rotating stent with a coating substance;
drying the coating substance including applying a gas to the surface of the stent after the spraying step and before a next spraying step; and
repeating the spraying and drying steps until the coating is applied to the stent.

5. The method of claim 4, wherein the arm elements include arms extending at an acute angle from the surface.

6. A method for coating a stent having a longitudinal axis, comprising:
supporting the stent on elongate arm elements extending as cantilevers from a surface of a support member, the support member being coupled to a motor;
rotating the stent about the longitudinal axis while the stent is supported by the arm elements; and
applying a coating to the stent, including the steps of
spraying the rotating stent with a coating substance;
drying the coating substance including applying a gas to the surface of the stent after the spraying step and before a next spraying step; and
repeating the spraying and drying steps until the coating is applied to the stent;
wherein the arm elements include parallel arms with spheres at the ends to support the stent.

7. The method of claim 4, further providing a first motor and a second motor, the first motor translating the stent and the second motor rotating the stent, wherein the stent is rotated and/or translated during the applying a coating step.

8. The method of claim 4, wherein the drying step occurs during the applying a coating step.

9. The method of claim 4, wherein the spraying step includes spraying the rotating stent with a polymer-drug substance and a solvent.

10. The method of claim 4, further including supporting a first end of the stent on the elongate arm elements and supporting a second end of the stent on a second support member.

11. The method of claim 10, further including supporting the second end of the stent on elongate arm elements extending from a second surface of the second support member.

12. The method of claim 11, wherein a mandrel extends between the first and second support members and the stent to mandrel rotation rate is 1:1 during the spraying step.

13. The method of claim 1, wherein the arm elements do not touch each other.

14. The method of claim 1, the providing step further including providing a space between tips of the elongate arm elements.

15. The method of claim 1, the providing step further including a mandrel that passes between tips of a first and second elongate arm element.

16. The method of claim 4, wherein the arm elements do not touch each other.

17. The method of claim 4, the providing step further including providing a space between tips of the elongate arm elements.

18. The method of claim 4, the providing step further including a mandrel that passes between tips of a first and second elongate arm element.

* * * * *